United States Patent [19]

Dawson

[11] Patent Number: 4,537,604
[45] Date of Patent: Aug. 27, 1985

[54] ABRASIVE AGGLOMERATES FOR USE IN SCOURING CLEANING COMPOSITIONS

[75] Inventor: Peter L. Dawson, Upton-by-Chester, England

[73] Assignee: Lever Brothers Company, New York, N.Y.

[21] Appl. No.: 528,186

[22] Filed: Aug. 31, 1983

[30] Foreign Application Priority Data

Sep. 1, 1982 [GB] United Kingdom ............... 8224944
Jul. 19, 1983 [GB] United Kingdom ............... 8319441

[51] Int. Cl.$^3$ .............................................. C09K 3/14
[52] U.S. Cl. .................................. 51/298; 51/309; 252/88; 252/174.23; 252/174.25
[58] Field of Search ............... 51/298, 309; 252/88, 252/140, 155, 174.23, 174.25

[56] References Cited

U.S. PATENT DOCUMENTS

| | | | |
|---|---|---|---|
| 3,387,956 | 6/1968 | Blue | 51/298 |
| 3,955,942 | 5/1976 | Cordon et al. | 51/298 |
| 4,005,027 | 1/1977 | Hartman | 252/155 |
| 4,089,943 | 5/1978 | Roberts et al. | 51/298 |
| 4,111,666 | 9/1978 | Kalbow | 51/298 |
| 4,122,025 | 10/1978 | Kiewert et al. | 252/155 |
| 4,157,387 | 6/1979 | Benedict | 51/298 |
| 4,181,633 | 1/1980 | Colodney et al. | 252/174.25 |
| 4,302,347 | 11/1981 | Straw et al. | 252/155 |
| 4,355,067 | 10/1982 | Neveu | 51/298 |
| 4,396,525 | 8/1983 | Rubin et al. | 252/113 |

FOREIGN PATENT DOCUMENTS 955081 4/1964 United Kingdom .
1345119 1/1974 United Kingdom .

Primary Examiner—Paul Lieberman
Assistant Examiner—Willie Thompson
Attorney, Agent, or Firm—Milton L. Honig; James J. Farrell

[57] ABSTRACT

Scouring cleaning compositions are disclosed in which the abrasive agent consists of agglomerates of finely divided abrasive material and an organic binder for agglomerating such material. Compositions of the invention have good soil-removing properties and improved non-scratching behavior. They are useful as powdered or liquid household products as well as skin-cleaning products.

23 Claims, No Drawings

ABRASIVE AGGLOMERATES FOR USE IN SCOURING CLEANING COMPOSITIONS

The present invention relates to scouring cleaning compositions in dry or liquid form. It is concerned with compositions in which the abrasive material does not scratch or damage weak or soft materials but still exhibits excellent abrasive properties.

In the prior art, many scouring cleaners have been described. Normally, scouring compositions consist of one or more abrasive materials, usually water-insoluble, one or more inorganic salts, usually alkaline, and optionally one or more surface-active materials. Other compounds, for example oxidizing or reducing bleaches, stabilizers for any bleach constituent, perfume and agents especially directed to thickening, colouring, complexing, soil-suspending, can be included if desired.

The abrasive particles conventionally used are irregularly shaped, powdered or ground materials of average particle diameter of about 10 to 100 microns.

However, it is not desirable for the abrasive particles to scratch or damage the substrate from which soil has to be removed and thus they are selected by virtue of their being softer than the substrate, yet harder than the soils they are intended to remove.

Cheap and effective minerals selected from abundantly occurring constituents of the earth's crust, such as calcite, chalk, marble, dolomite, feldspar or quartz have been found suitable for cleaning ceramic, stone, vitreous enamel, chromium and stainless steel surfaces, but these abrasives are not suitable for cleaning more sensitive surfaces like perspex, paint work, polished woodwork, melamine-faced laminates and PVC, without severe concurrent scratching and dulling. Reducing the particle size of the abrasive to below 10 microns reduces scratching and dulling considerably, but soil removal is also considerably diminished.

The utilisation of softer particles in the preferred size range for cleaning may prevent substrate damage, but for example a soft mineral such as pure gypsum (calcium sulphate) is too weak to abrade typical soils efficiently and has the further disadvantage of being soluble in water, whereas the pure, naturally occurring clays and talcs break down to platelets very easily and neither scratch nor clean. The use of powdered polymers as abrasives does satisfy the criteria for good detergency of the soils found on modern plastic surfaces with little or no substrate damage. Polyethylene, polystyrene and polyvinylchloride powders have been suggested as suitable. These, however, are relatively very expensive for use in general household or institutional cleaning compositions and are further ecologically undesirable agents in terms of disposal and waste of valuable natural resources.

It has now been found that non-scratching abrasive particles having good cleaning properties can be made by agglomerating substantial proportions of finely divided mineral material with organic binder. Accordingly, it has been found that compositions containing said abrasive agglomerates have good soil-removing properties, yet are substantially non-scratching.

It has also been found that inclusion of said abrasive agglomerates in a cosmetically acceptable base provides a very mild cosmetic scouring composition which does not roughen or abrade the human skin.

By choosing a binder with the correct mechanical properties, particles can be made by using simple technology, which are large enough and strong enough to abrade soils, such as grease, jam, bath scum, etc., yet deform or disintegrate when the substrate is contacted. In a preferred embodiment the present invention provides non-scratching, scouring cleaning compositions in which the abrasive agent is formed by friable, deformable agglomerates consisting essentially of abrasive material, the particles of which have initial sizes all below 20 microns, at least 80% by weight thereof being below 10 microns, and an organic binder agglomerating said abrasive material.

The abrasive materials that can be used in the compositions according to the present invention may be any of those known in the prior art.

It is preferred that the maximum particle size is 10 microns, but it can be tolerated that up to 20% by weight of the mineral has sizes above 10 microns, provided all sizes are below 20 microns.

Preferably 25 to 80% by weight of the abrasive particles have sizes below 2 microns. As particles of such smallness are non-scratching, irrespective of their hardness on Moh's scale, a wide range of minerals may be used. Thus, dolomites, aragonites, feldspars, various forms of silica, aluminas, gypsum, clays, kaolins, etc., or mixtures thereof are all suitable basic abrasive materials. Particularly suitable is calcite, for instance limestone, chalk or marble, such as those forms of calcite referred to in British Patent Specification No. 1 345 119.

An important economical advantage of the present invention is the possibility to use and upgrade poor mineral material. Thus, material rejected for current abrasive cleaners on the grounds of scratching or being too soft when used at a conventional particle size of e.g. 50 microns, may be produced or obtained very cheaply at sizes below 10 microns for use in the present invention.

In choosing suitable agglomerating agents, both mechanical and chemical considerations should be taken into account.

From the mechanical point of view, suitable binders for the present invention are selected on the basis of two criteria applied to a cast bar of the agglomerate:

(a) the flexural strength and (b) the elastic and plastic properties. These properties are influenced by the binder and its ratio to the mineral in a complicated manner and are believed to be important for the non-scratching behaviour of the agglomerated particles. Thus, the scratch-determining property is both a function of the elasticity/plasticity of the agglomerates, i.e. the amount of deformation that is possible when the agglomerates are brought into contact with the substrate, and the friability relating to the mechanical strength of the agglomerates, i.e. the tendency to break when brought into contact with the substrate.

The flexural strength of the agglomerate can be measured by means of a 3-point breaking force test. In this test, semi-circular cross-section bars of the agglomerated material with radius 4 mm are supported horizontally (curved side up) on piers 17 mm apart. A gradually increasing downward force is applied to the middle of the bar until it breaks. Materials exhibiting flexural strengths above about 1.5 kg have been found suitable to provide abrasive powders of sufficient strength to clean typical soils efficiently. Flexural strengths of about 3 to 6 kg are preferred and in particular 4 to 5.5 kg. The achievement of such strengths in combination with a non-scratching behaviour has been found to be by way of careful selection of the organic binder with due regard to its elastic or plastic behaviour and the selection of particle size distributions giving optimal packing, which can be suitably quantified by the microhardness of the agglomerates. In general, the agglomerates should have a microhardness on the Vickers hardness scale in the range of 3 to 10, preferably 6 to 8.

An important consideration in selecting suitable binders is also the chemical stability of the agglomerates, for instance when used in an aqueous alkaline surfactant suspending medium.

Binders that satisfy the above criteria and have adequate adhesive power to form agglomerates with high mineral/binder ratios, preferably are waxes exhibiting some degree of reactive character towards the mineral constituent, either owing to some e.g. carboxylic acid groups in the wax molecule or to the external addition of minor amounts of oil-soluble polar materials, such as e.g. quaternary ammonium compounds, anionic higher fatty acids, waxes with high acid numbers and higher molecular weight soaps and anionic surfactants. The degree of polarity introduced into the organic binder system is critical in that an amount is required sufficient to maximise particle binding and waterproofing, whereas excess leads to susceptibility to e.g. aqueous alkaline surfactant media in which these agglomerated abrasives may have to operate.

Accordingly, suitable organic binders giving agglomerates with flexural strengths in the preferred range of about 3 to 6 kg are waxes selected, either singly or in blends, from the group consisting of:

(a) Neutral paraffin waxes of both the predominantly straight-chain and the highly branched type (the micro-crystalline waxes) with melting points between 40° and 90° C. Also lightly oxidized derivatives of those waxes up to acid numbers of about 20 (mg KOH per gram wax).

(b) Montan ester waxes with melting points of between about 70° and 100° C. with acid numbers up to about 20.

(c) Low molecular weight polyethylene waxes (mol. weight about 2000) with melting points between about 100° and 125° C. and acid numbers up to about 20.

(d) Higher polyalkylenes, e.g. polypropylenes, polybutenes, with distinct melting points in the range 60°–150° C.

(e) Fully hardened triglyceride oils, e.g. tallow, vegetable and fish oils.

Also suitable are waxes which give agglomerates with flexural strengths above 1.5 kg, but outside the range of about 3 to 6 kg, finding application in the specialized cleaning of very sensitive materials, such as e.g. delicate paint work, or tougher surfaces, such as e.g. melamine laminates.

They include paraffin waxes with melting points of below 50° C., such as e.g. cetyl/stearyl alcohols or stearyl stearate, giving flexural strengths in the range of 1.5 to 3 kg, and waxes giving strengths above 6 kg or Vickers hardness above 10, such as e.g. carnauba ester wax and polyethylene waxes with higher molecular weights (above 2500) and melting points above 125° C.

It is often preferred to introduce degrees of either anionic or cationic polar behaviour into the wax binder systems, depending on the chemical properties of the mineral material selected. Oil-soluble cationic compounds are preferred for talcs, kaolins and silicas, whereas anionic compounds are preferred for marbles, chalks, feldspars, dolomites and gypsum. Some minerals, e.g. the feldspars and carbonates, exhibit amphoteric behaviour.

Suitable anionic oil-soluble polar compounds include fatty acids which preferably have more than 18 carbon atoms in the alkyl chain; oxidized paraffins preferably with chain lengths of 20 to 40 carbon atoms and acid numbers of about 100 to 150; polyethylene waxes (mol. weights of about 2000) preferably having acid numbers of about 10 to 30; montanic acids preferably having acid numbers of about 100 to 150; montan acid esters preferably having acid numbers of about 35 to 100; and high molecular weight alkyl sulphates and sulphonates, such as e.g. di($C_{14}$–$C_{15}$)sulphosuccinate.

Suitable cationic compounds include higher fatty amines, e.g. stearylamine, and higher molecular weight alkyl(aryl)quaternaries, e.g. di-lauryl-di-methyl ammonium chloride and di-stearyl-di-methyl ammonium chloride.

With neutral waxes, preferably the oil-soluble poor compounds are incorporated at a level of 1 to 20%, more preferably 2 to 20% and most preferably 4 to 10% by weight of the wax. If waxes are employed with some polar character themselves, accordingly less of the polar additive has to be incorporated. Preferably the wax blend (i.e. the wax plus optionally the polar compound) has an initial acid number of between 1 and 10 or even between 2 and 5.

Generally the oil-soluble polar compounds are blended with the molten wax prior to the addition of the fine mineral material.

An advantageous method of introducing a degree of polarity into the wax system is in situ production of oxidized paraffin, wherein the paraffin wax and mineral are mixed together and heated to temperatures in excess of 120° C. with good air contact. The paraffin wax acids being formed during the heating then react with the mineral to provide optimal particle binding.

Suitable binding systems also are high molecular weight polymers (or mixtures thereof) satisfying the physical and chemical criteria stated above. Such compounds selected from the group of lightly carboxylated polymers based on styrene, alkylacrylic esters, ethylene, vinyl chloride, vinylidene chloride or butadiene provide suitable mineral/binder matrices.

It is preferred that the polymer binders exhibit some polar behaviour so as to maximize binding to the mineral. Preferably, the binding groups, e.g. of the carboxylic or amine type, are chemically attached to the polymer backbone, which has the additional and advantageous possibility of cross-linking, thus improving solvent resistance and strength.

The weight ratio between the abrasive material and the binder can be varied widely depending on the type of binder used. For waxes the mineral/binder ratio will normally be between 1:1 and 8:1. The lower limit of this ratio is primarily dictated by cost considerations, but also stems from the fact that the intrinsic strength of waxes is increased (usually about 2–3 fold) by admixing finely powdered abrasive material, but only at ratios of 50% by weight or more. The upper limit is that beyond which the mechanical strength of the wax system falls off to zero. Preferably, weight ratios of mineral to wax blend are between 4:1 and 5.5:1.

The polymer emulsion- or solution-bound mineral aggregate systems are not subject to the upper mineral limit for waxes of about 85–90% by weight. They do not melt and fill the interstitial voids as do the waxes, but, being sticky, they spot-glue the mineral particles together when the solvent phase is removed above the minimum film-forming temperature for that polymer. Because of the higher tensile strengths exhibited by polymers, these systems retain acceptable mechanical strengths up to mineral/binder weight ratios of 97:3.

If the binder has a definite melting point, e.g. the waxes, then agglomerates with up to about 5 to 6 parts by weight of mineral to 1 part of molten wax are easily made by hot-mixing to a slurry which on cooling may be milled to the desired particle size range. Alternatively, pan-granulation techniques, flaking, extrusion or spray-cooling of the slurry may be employed prior to milling.

At higher mineral to binder ratios there is not enough molten liquid phase to fill the interstices between the particles and mobile slurries cannot be made. This is solved by using solutions or emulsions of binder to make a slurry with the mineral, followed by heat-drying to drive off the solvent or water and coalesce the wax or polymeric particles in the agglomerating matrix. The cast or spray-dried solids are then milled to the desired particle size by using conventional techniques. These particles are porous when dried and the voids left by the evaporated solvent fill up with solution when wetted. Agglomerates can be produced having any preferred size range or shape. Abrasive sizes can range from 10 to 500 microns or more if so desired. It is preferred that particle sizes are in the range from about 10 to about 200 microns, distributions preferably having mean sizes from about 75 to about 125 microns.

In scouring compositions, generally also one or more surface-active agents are included. Suitable as surfactants in the compositions of the present invention are any of the detergent-active compounds normally used in scouring cleansers, including anionic, nonionic, cationic, zwitterionic and amphoteric compounds.

Suitable anionic surfactants are alkali metal or alkanolamine salts of $C_{12}-C_{18}$ branched or straight chain alkyl aryl sulphonates, of $C_{12}-C_{18}$ paraffin sulphonates, of $C_8-C_{12}$ branched or straight chain alkyl sulphonates, of $C_{10}-C_{18}$ alkyl $EO_{1-10}$ sulphates, of sulphosuccinates, of $C_{10}-C_{24}$ fatty acid soaps, etc. It is often desirable to include also a nonionic or zwitterionic detergent material, especially in the liquid type of scouring compositions. Suitable examples of nonionic detergents are water-soluble condensation products of ethylene oxide and/or propylene oxide with linear primary or secondary $C_8-C_{18}$ alcohols, with $C_8-C_{18}$ fatty acid amides or fatty acid alkylolamides (both mono- and diamides), with $C_9-C_{18}$ alkyl phenols and so on. The alkoxylated $C_8-C_{118}$ fatty acid mono- and dialkylolamides should contain more than one alkylene oxide unit, for instance they should be condensed with e.g. 2-5 moles of alkylene oxide such as ethylene oxide. Fatty acid mono- or dialkylolamides in which the fatty acid radical contains 10-16 carbon atoms are also suitable nonionics, such as e.g. cocofatty acid monoethanolamide. Suitable zwitterionic detergents are trialkylamine oxides having one long alkyl chain ($C_8-C_{18}$) and two short alkyl chains ($C_1-C_4$), betaines and sulphobetaines. Other surfactants and combinations of surfactants are those referred to for use in scouring cleanser compositions described in British Patent Specification Nos. 822 569, 955 081, 1 007 342, 1 044 314, 1 167 597, 1 181 607, 1 262 280, 1 303 810, 1 308 190, 1 345 119 and 1 418 671.

It is often desirable that scouring compositions of the present invention contain adjuncts, especially builder salts such as alkali metal silicates, carbonates, orthophosphates, pyrophosphates and polyphosphates, nitrilotriacetates, citrates, and mixtures thereof, colouring agents, perfumes, fluorescers, hydrotropes, soil-suspending agents, bleaching agents and precursors therefor, enzymes, opacifiers, germicides, humectants and salt electrolytes such as those referred to in the above patent specifications.

Particularly valuable are scouring compositions that are free-flowing powders. Such cleansers can contain from 0.1 to 40% by weight of surfactant, from 5 to 99% by weight of abrasive powder and from 0 to 95% by weight of scouring cleanser adjuncts. Also particularly valuable are scouring cleansers that are pasty or pourable aqueous liquid compositions. Such cleansers can contain from 0.1 to 50% by weight of surfactant and from 5 to 60% by weight of abrasive powder, the remainder being scouring cleanser adjuncts and water. Preferably the abrasive powder is dispersed in the aqueous medium of the cleanser, and the aqueous medium comprises a micellar or polymeric suspending system which maintains the powder in dispersion. Suitable aqueous media are those described in British Patent Specification Nos. 1 167 597, 1 181 607, 1 262 280, 1 303 810, 1 308 190 and 1 418 671.

The agglomerate compositions are suitable for long-term stability in aqueous suspending media, particularly those using non-phosphate neutral or alkaline electrolytes. Increased phosphate tolerance may be provided by including in the wax blend the higher levels of carboxylic acids and/or the higher molecular weight members of the group of oil-soluble polar compounds, or the higher molecular weight neutral paraffin and polyethylene waxes.

Alternatively waterproofers such as the terpene hydrocarbon resins, e.g. piccolyte S100 ex Hercules Inc., may be added to the wax blend in minor amounts.

The invention will further be described by way of examples, in which parts and percentages are by weight unless indicated otherwise.

EXAMPLE I (Liquid)

The following abrasive agglomerates were prepared for use in a liquid scouring composition.

|  | % |
| --- | --- |
| 1. | |
| Paraffin wax m.pt 60° C. | 16.3 |
| Montan acid ester (acid number 90) | 0.7 |
| Crushed marble (average particle size 2μ, 100% less than 10μ) | 83 |
| Acid number of wax blend (initially) | 3.7 |
| Strength (¼ round bar-flexural) | 5.0 kg |
| Hardness (on the Vickers scale) | 7.0 |
| 2. | |
| Paraffin wax m.pt 60° C. | 15.3 |
| Oxidized polyethylene wax (m.pt 100° C., acid number 25) mol · wt ~2000 | 1.7 |
| Crushed marble (average particle size 2μ, 100% less than 10μ) | 83 |
| Acid number of wax blend (initially) | 2.5 |
| Strength (¼ round bar-flexural) | 5.5 kg |
| hardness (on the Vickers scale) | 6.0 |
| 3. | |
| Paraffin wax m.pt 60° C. | 16.4 |
| Montan acid (acid number 145) | 0.6 |
| Crushed marble (average particle size 2μ, 100% less than 10μ) | 83 |
| Acid number of wax blend (initially) | 5.1 |
| Strength (¼ round bar-flexural) | 4.5 kg |

-continued

|  | % |
|---|---|
| Hardness (on the Vickers scale) | 7.5 |
| Liquid scouring composition: |  |
| Coconut diethanolamide | 3 |
| Na alkylbenzene sulphonate | 3 |
| trisodium citrate dihydrate | 3 |
| fine chalk (100% less than 5μ) | 2.5 |
| agglomerate (average size 90μ) | 40 |
| water | balance |

EXAMPLE II

|  | 1 (Powder) | 2 (Liquid) | 3 (Liquid) |
|---|---|---|---|
| Na alkylbenzene sulphonate | 2 | 3 | 3 |
| Lauric diethanolamide | — | 3 | 3 |
| Trisodium phosphate | 3 | — | — |
| Sodium tripolyphosphate | — | 6 | 6 |
| Perfume | 0.2 | 0.3 | 0.3 |
| Calcite[1] | — | — | 20 |
| Calcite[1]/Montan Wax[2] agglomerate[3] | 94.8 | 40 | 20 |
| Water | — | 47.7 | 47.7 |

[1] ex chalk, particle distribution:
0% > 20μ
14% > 10μ
36% > 5μ
40% < 2μ
[2] Hoechst Wax F: acid number 8, mpt 80° C.
[3] Weight ratio 5:1 (mineral/binder): bar breaking strength 5.5 kg. Milled and sieved through 180μ mesh: average particle size ~90μ.

EXAMPLE III (Liquid)

|  |  |
|---|---|
| Na alkylbenzene sulphonate | 3 |
| Lauric diethanolamide | 3 |
| Sodium tripolyphosphate | 6 |
| Perfume | 0.3 |
| Calcite[1] | 10 |
| Calcite[1]/polyethylene wax[2] agglomerate[3] | 35 |
| Water | 42.7 |

[1] ex marble, particle distribution:
0% > 10μ
12% > 5μ
50% < 2μ
[2] ex Hoechst. Mol · wt 2000, m · pt 120° C., acid number zero; with 1.7% stearic acid added, acid number of wax blend 3.4.
[3] Weight ratio 4.5:1 (mineral/binder): bar breaking strength 4.4 kg and Vickers hardness 7.5. Milled and sieved through 200μ mesh: average particle size 100μ.

EXAMPLE IV (Paste)

|  |  |
|---|---|
| Potassium coconut soap | 4% |
| Calcite[1]/paraffin wax[2] agglomerate[3] | 78% |
| Water, perfume, colour | 18% |

[1] ex chalk, particle distribution:
0% > 20μ
6% > 10μ
28% > 5μ
35% < 2μ
[2] m · pt 67° C., acid number zero: with 1.6% stearic acid added.
[3] Weight ratio 5:1 (mineral/binder): bar breaking strength 4.0 kg. Milled and sieved to 90μ average diameter.

EXAMPLE V (polymer-bound calcite in powder composition)

A stiff aqueous slurry of 1.5 parts of a 50% solids emulsion of a styrene-acrylic copolymer with 9 parts of a finely ground marble, mean particle size 2μ, was prepared. The paste was spread on a tray and dried in an oven at 50° C. (above the MFFT for the polymer). A cast semi-circular cross-section bar showed a dry strength of 3.7 kg.

The dried agglomerate was broken up and milled to a range of particle sizes averaging about 90μ. This powder was incorporated in the following composition:

|  | % |
|---|---|
| Na alkylbenzene sulphonate | 2 |
| Trisodium phosphate | 3 |
| Perfume | 0.2 |
| Polymer/calcite agglomerate | 94.8 |
| (7.7% polymer; bar breaking strength 3.7 kg.) |  |
| Calcite particle distribution: | 0% > 10μ |
|  | 12% > 5μ |
|  | 50% < 2μ |

The composition, slurried with a little water, cleaned a model waxy soil (simulating bath scum) from a piece of virgin perspex, efficiently and with no trace of damage.

EXAMPLE IV (Scouring powder with chlorine)

A scouring powder providing chlorine in addition was also made:

|  | % |
|---|---|
| Na alkylbenzene sulphonate | 2 |
| Sodium phosphate hypochlorite | 10 |
| Perfume | 0.2 |
| Dolomite[1]/wax blend[2] agglomerate[3] | 87.8 |

[1] particle distribution:
0% > 20μ
10% > 10μ
27% > 5μ
30% < 2μ
[2] 80% paraffin wax m · pt 60° C., acid number zero; 20% polyethylene wax m · pt 105° C., mol · wt 2000, acid number 17.
[3] 4.5:1 wt ratio (mineral/binder): bar breaking strength 4.5 kg. Milled to 100μ average diameter.

Good cleaning, excellent bleaching and germicidal effects and minimal damage to plastic surfaces were obtained.

EXAMPLE VII

A very mild, but efficient, liquid scouring composition was prepared using a "light kaolin" aggregate bound with a 95:5 paraffin wax/micro-crystalline wax blend, plasticised with a little di-hardened tallow dimethyl ammonium chloride.

The optimum ratio of about 70:30 kaolin powder to wax binder is lower than that found with e.g. feldspar, dolomite, quartz, calcite, etc., owing to the plate-like morphology of the clay. The milled aggregate of about 100μ average particle size could be incorporated into either micellar surfactant/electrolyte or polymeric surfactant suspending systems at about 40% by weight of the total composition, for example:

|  | % |
|---|---|
| Tallow alcohol 10 EO | 3.3 |
| Diethanolamine | 1.7 |
| Copolymer of 1 mole methacrylic acid with 2 moles ethyl acrylate | 0.5 |
| Kaolin[1]/paraffin wax[2] agglomerate[3] | 44 |

| | % |
|---|---|
| -continued | |
| Water, perfume, etc. | to 100.0 |

[1] Light grade,
0.5% > 10μ
75% < 2μ
[2] Blend of paraffin wax m - pt 67° C., acid number zero (95%) with micro-crystalline wax m - pt 85° C., acid number zero (5%) with 1–2% (on wax blend) of commercial distearyl dimethyl ammonium chloride.
[3] 2.5:1 wt ratio (mineral/binder); bar breaking strength 2.8 kg. Milled to 95μ average diameter.

This composition, in addition to giving efficient cleaning without damage to plastic surfaces, is with slight modification also suitable for use as a heavy duty hand cleanser.

Unlike conventionally used herein abrasive- or solvent-based hand cleansers, the skin is not roughened or abraded and no residual solvent smells occur.

Modifications to the above composition for safe prolonged skin contact include reducing the level of diethanolamine to give a pH of 8–9, or replacing the amine/polymer thickening system by a neutral water-soluble gum. Alternatively, known mild surfactants, e.g. alkyl amine oxides, soaps, etc., may be thickened with non-toxic gums, alginates, etc. to make suspending gels containing the agglomerates of the invention.

The invention has been described with respect to descriptions and illustrations of specific embodiments thereof, but is not to be limited to these, since it is evident that one skilled in the art will be able to utilize substitutes and equivalents without departing from the spirit of the invention or going beyond its scope.

I claim:

1. Scouring cleaning compositions comprising from 5 to 99% by weight of an abrasive agent consisting of agglomerates of finely divided abrasive material having no particles of initial size above 20 micrometers, at least 80% by weight thereof being of initial size below 10 micrometers, and an organic binder for agglomerating such material, from 1 to 20% by weight of the binder being an oil-soluble anionic or cationic polar compound; the flexural strength of the agglomerates being above 1.5 kilograms.

2. Compositions according to claim 1, in which the abrasive material comprises no particles of initial size above 10 micrometers.

3. Compositions according to claim 1, in which 25 to 80% by weight of the particles of the abrasive material have initial sizes of below 2 micrometers.

4. Compositions according to claim 1, in which the abrasive material is calcite.

5. Compositions according to claim 1, in which the abrasive agglomerates have a flexural strength of between 3 and 6 kg.

6. Compositions according to claim 5, in which the abrasive agglomerates have a flexural strength of between 4 and 5.5 kg.

7. Compositions according to claim 1, in which the abrasive agglomerates have a micro-hardness on the Vickers scale of between 3 and 10.

8. Compositions according to claim 7, in which the abrasive agglomerates have a micro-hardness on the Vickers scale of between 6 and 8.

9. Compositions according to claim 1, in which the organic binder comprises a wax.

10. Compositions according to claim 9 in which the wax is a straight or branched chain paraffin wax with a melting point of between 40° C. and 90° C.

11. Compositions according to claim 9, in which the wax has an acid number up to about 20.

12. Compositions according to claim 1, in which the organic binder comprises from 1 to 20% by weight of the polar compound.

13. Compositions according to claim 12, in which the organic binder comprises from 2 to 20% by weight of the polar compound.

14. Compositions according to claim 13, in which the organic binder comprises from 4 to 10% by weight of the polar compound.

15. Compositions according to claim 9, in which the organic binder has an initial acid number of between 1 and 10.

16. Compositions according to claim 15, in which the organic binder has an initial acid number of between 2 and 5.

17. Compositions according to claim 16, in which the weight ratio between the abrasive material and the organic binder is within the range of from 1:1 to 8:1.

18. Compositions according to claim 17, in which the weight ratio between the abrasive material and the organic binder is within the range of from 4:1 to 5.5:1.

19. Compositions according to claim 1, in which the organic binder comprises a high molecular weight polymer.

20. Compositions according to claim 19, in which the weight ratio between the abrasive material and the organic binder is within the range of from 1:1 to 97:3.

21. Particulate scouring compositions according to claim 1, comprising 0.1 to 40% by weight of a detergent surfactant and 5 to 99% by weight of the abrasive agent, the balance being conventional scouring cleanser adjuncts.

22. Liquid scouring compositions according to claim 1, comprising 0.1 to 50% by weight of a detergent surfactant and 5 to 60% by weight of the abrasive agent, the balance being water and conventional liquid scouring cleanser adjuncts.

23. Skin cleansing compositions according to claim 1, comprising 5 to 60% by weight of the abrasive agent in a cosmetically acceptable base.

* * * * *